United States Patent
Marian, Jr.

(10) Patent No.: US 6,659,955 B1
(45) Date of Patent: Dec. 9, 2003

(54) MEDICAL DIAGNOSTIC ULTRASOUND IMAGING SYSTEM TRANSMITTER CONTROL IN A MODULAR TRANSDUCER SYSTEM

(75) Inventor: Vaughn R. Marian, Jr., Saratoga, CA (US)

(73) Assignee: Acuson Corp., Mountain View, CA (US)

( * ) Notice: Subject to any disclaimer, the term of this patent is extended or adjusted under 35 U.S.C. 154(b) by 0 days.

(21) Appl. No.: 10/185,472

(22) Filed: Jun. 27, 2002

(51) Int. Cl.[7] ............................................. A61B 8/00
(52) U.S. Cl. ..................................... 600/459; 600/437
(58) Field of Search ................... 604/323, 95; 600/437, 600/443, 459, 461, 460

(56) References Cited

U.S. PATENT DOCUMENTS

| | | |
|---|---|---|
| 5,520,187 A | 5/1996 | Snyder |
| 5,590,658 A | 1/1997 | Chiang et al. |
| 5,617,866 A * | 4/1997 | Marian, Jr. .................. 600/459 |
| 5,634,464 A * | 6/1997 | Jang et al. .................. 600/467 |
| 5,797,848 A | 8/1998 | Marian et al. |
| 5,820,549 A | 10/1998 | Marian, Jr. |
| 5,846,097 A | 12/1998 | Marian, Jr. |
| 5,865,650 A | 2/1999 | Marian, Jr. et al. |
| 5,882,310 A | 3/1999 | Marian, Jr. |
| 5,913,688 A | 6/1999 | Marian, Jr. |
| 6,165,164 A * | 12/2000 | Hill et al. .................... 604/523 |

* cited by examiner

Primary Examiner—Francis J. Jaworski
Assistant Examiner—Maulin Patel

(57) ABSTRACT

The preferred embodiments described herein provide medical diagnostic ultrasound imaging system transmitter control in a modular transducer system. With these preferred embodiments, transmitters in a medical diagnostic ultrasound imaging system are enabled only when contacts in a scan head are electrically coupled with contacts in a receptacle assembly of a modular transducer system. This prevents high voltages from developing in the receptacle assembly when the scan head is removed from or is not fully engaged with the receptacle assembly. In one preferred embodiment, a detector is used to detect movement of a member comprising the contacts in the receptacle assembly. Other preferred embodiments are provided, and each of the preferred embodiments described herein can be used alone or in combination with one another.

17 Claims, 14 Drawing Sheets

MEDICAL DIAGNOSTIC ULTRASOUND IMAGING SYSTEM TRANSMITTER CONTROL IN A MODULAR TRANSDUCER SYSTEM

BACKGROUND

Conventional ultrasonic transducer assemblies are expensive, one-piece devices that include a scan head containing an acoustic array of piezoelectric transducer elements, an electrical connector that plugs into an ultrasound system, and a cable with a multitude of coaxial conductors connecting the transducer elements in the scan head with the connector. Because different transducer assemblies are normally required to provide optimum diagnostic performance on a wide variety of patients and procedures, multiple assemblies must normally be available. In practice, a health care provider selects a particular transducer assembly and attaches its connector to the ultrasound system. When the health care provider wants to use a different transducer assembly, he disconnects the transducer assembly from the ultrasound system and then connects the new one. Because the cables of conventional ultrasonic transducer assemblies are bulky and awkward to manipulate, changing from one transducer assembly to another can markedly slow the pace of an ultrasound examination. Storing and cleaning the cables can also be difficult.

The inventor of the present invention developed a "modular transducer system" as a convenient alternative to conventional ultrasonic transducer assemblies. Embodiments of the modular transducer system are described in U.S. Pat. Nos. 5,617,866 and 5,820,549. Generally, the modular transducer system comprises a detachable scan head that mates both mechanically and electrically to a receptacle assembly at one end of a cable connected to an ultrasound system. Because the scan head is conveniently changed at the receptacle assembly, the other end of the cable can either be hard wired into the imaging system or have a conventional system connector. A major advantage of the modular transducer system is that a single cable and receptacle assembly can support a multitude of scan heads. Since the single cable and receptacle assembly remains connected to the ultrasound system, the use of different scan heads merely requires one scan head to be interchanged with another, thereby avoiding the awkward manipulation of the cable assembly. Additionally, the use of a single cable and receptacle assembly to support a multitude of scan heads is particularly advantageous for future portable imaging systems.

Although there are many advantages associated with the modular transducer system, enhancements and additions to the modular transducer system can extend its potential diagnostic capabilities and utility.

SUMMARY

The present invention is defined by the following claims, and nothing in this section should be taken as a limitation on those claims.

By way of introduction, the preferred embodiments described below provide medical diagnostic ultrasound imaging system transmitter control in a modular transducer system. With these preferred embodiments, transmitters in a medical diagnostic ultrasound imaging system are enabled only when contacts in a scan head are electrically coupled with contacts in a receptacle assembly of a modular transducer system. This prevents high voltages from developing in the receptacle assembly when the scan head is removed from or is not fully engaged with the receptacle assembly. In one preferred embodiment, a detector is used to detect movement of a member comprising the contacts in the receptacle assembly. Other preferred embodiments are provided, and each of the preferred embodiments described herein can be used alone or in combination with one another.

The preferred embodiments will now be described with reference to the attached drawings.

DETAILED DESCRIPTION OF THE PRESENTLY PREFERRED EMBODIMENTS

The preferred embodiments presented herein describe several enhancements for a modular transducer system. It is important to note that these enhancements can be used alone or in combination with one another. Before turning to these enhancements, a general introduction to the modular transducer system is provided. Additional information about the modular transducer system can be found in U.S. Pat. Nos. 5,617,866; 5,797,848; and 5,820,549; each of which is hereby incorporated by reference.

The Modular Transducer System

Figure 1:
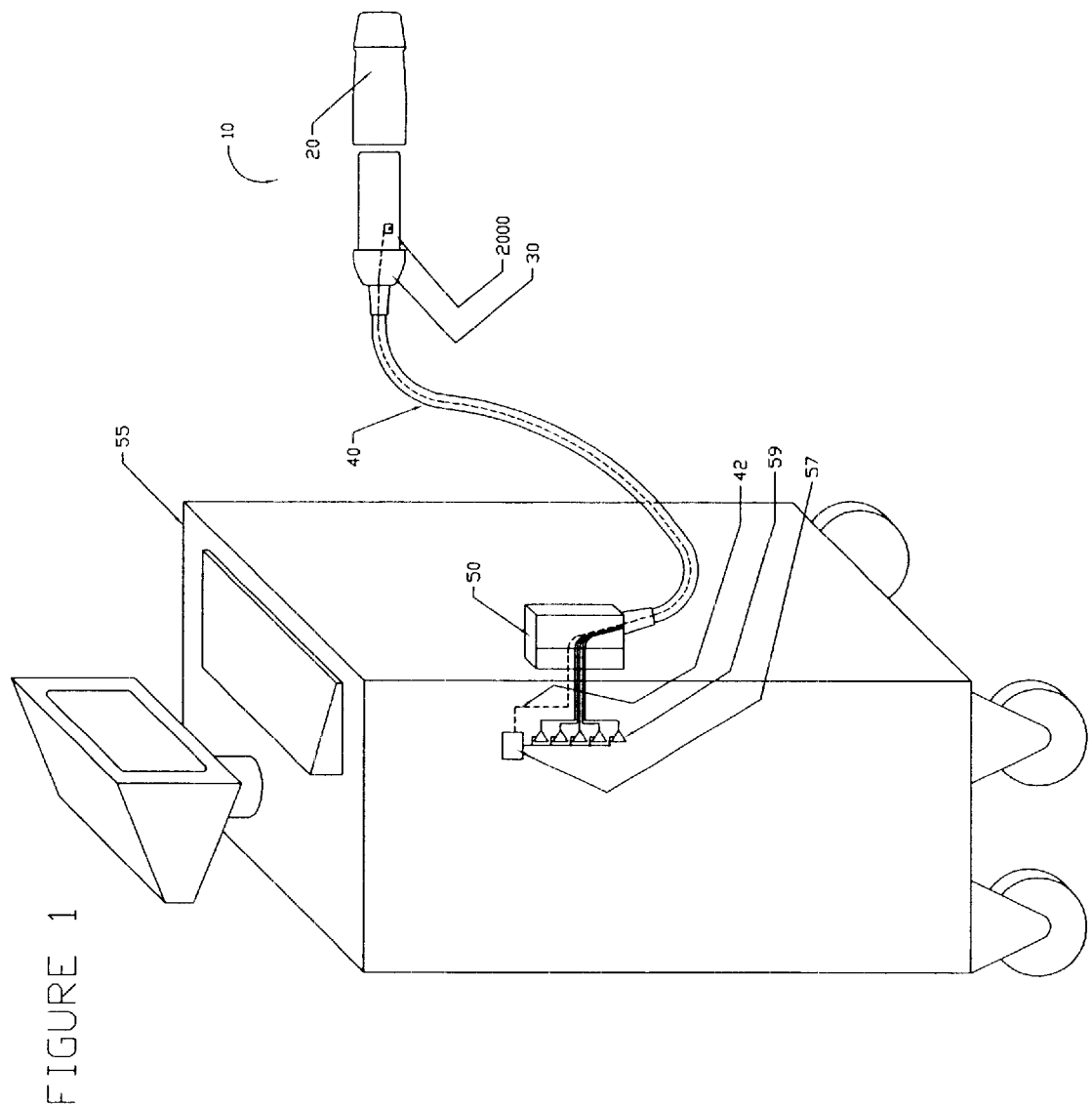
FIG. 1 is an illustration of a modular transducer system of a preferred embodiment.

Turning now to the drawings, FIG. 1 is an illustration of a modular transducer system 10 of a preferred embodiment. The modular transducer system 10 comprises a removable scan head 20 with an acoustic array of piezoelectric transducer elements, a receptacle assembly 30, a cable assembly 40, and a connector 50, which plugs into a medical diagnostic ultrasound imaging system 55. The cable assembly 40 houses numerous coaxial conductors that connect electrical contacts in the receptacle assembly 30 with electrical contacts in the connector 50. In an alternate embodiment, the connector 50 is not used, and the coaxial conductors are hard wired to the imaging system 55.

The scan head 20 comprises electrical contacts and conductors that connect each of the electrical contacts to respective piezoelectric transducer elements in the transducer array. When the scan head 20 is fully inserted into the receptacle assembly 30, the scan head 20 is mechanically coupled with the receptacle assembly 30, and the electrical contacts in the scan head 20 electrically couple with mating electrical contacts in the receptacle assembly 30. Accordingly, when the scan head 20 is properly coupled with the receptacle assembly 30, each element of the transducer array is coupled with a respective coaxial signal line in the cable assembly 40. With this connection made, the ultrasound system 55 can electrically communicate with the scan head 10 to independently control each transducer element. During an ultrasound examination, control circuitry 57 in the ultrasound system 55 enables a set of transmitters 59 to send electrical signals to the appropriate transducer elements to emit ultrasound acoustic waves into the body of a patient. The scan head 20 can be removed from the receptacle assembly 30 and interchanged with another scan head since the receptacle assembly 30 conveniently accepts a variety of different scan heads. As used herein, the phrase "coupled with" means directly coupled with or indirectly coupled with through one or more intervening (named or unnamed) components. As also used herein, the term "set" refers to a group of one or more than one member.

Figure 2:
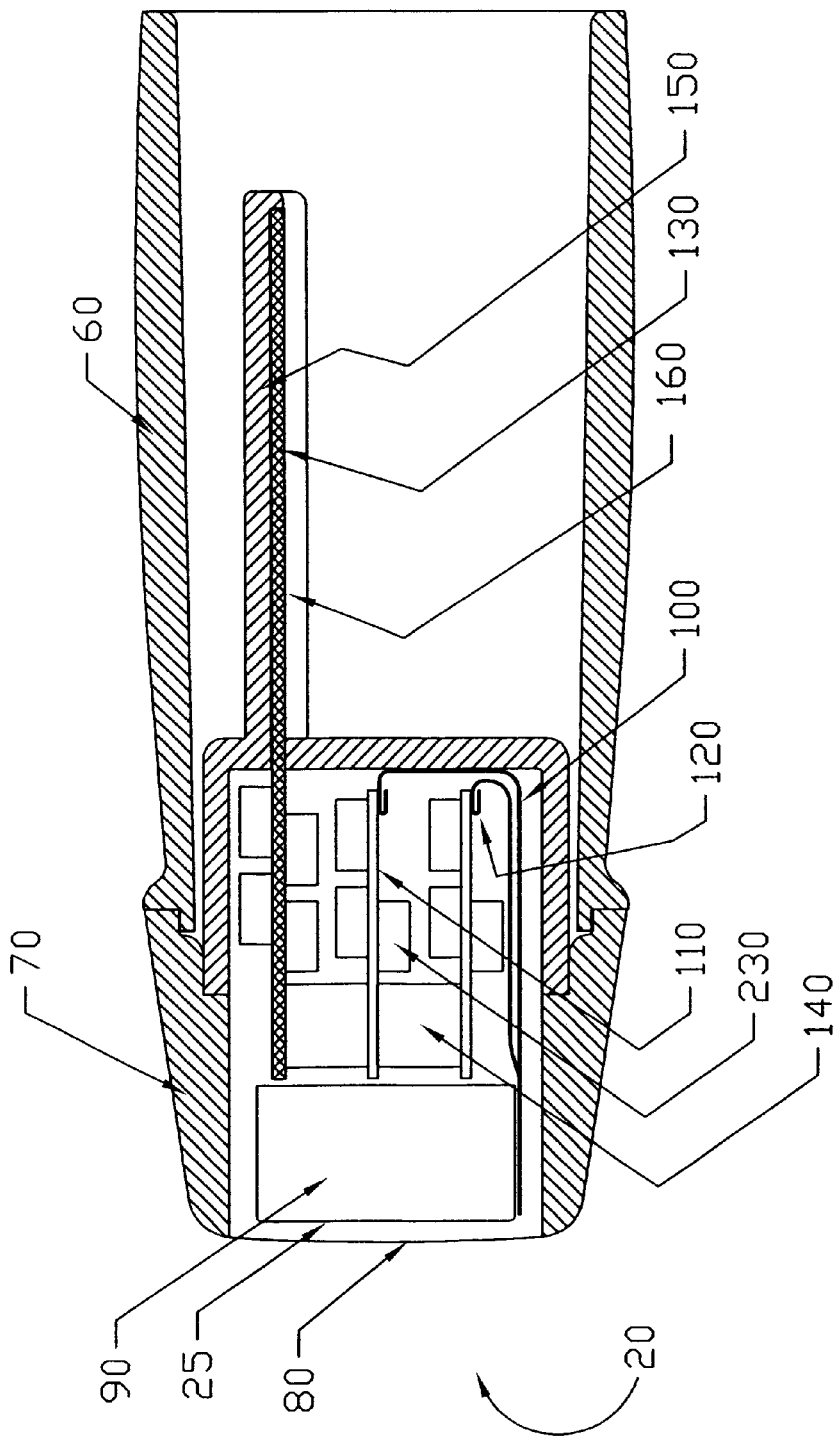
FIG. 2 is an illustration of a scan head of a preferred embodiment.
Figure 3:
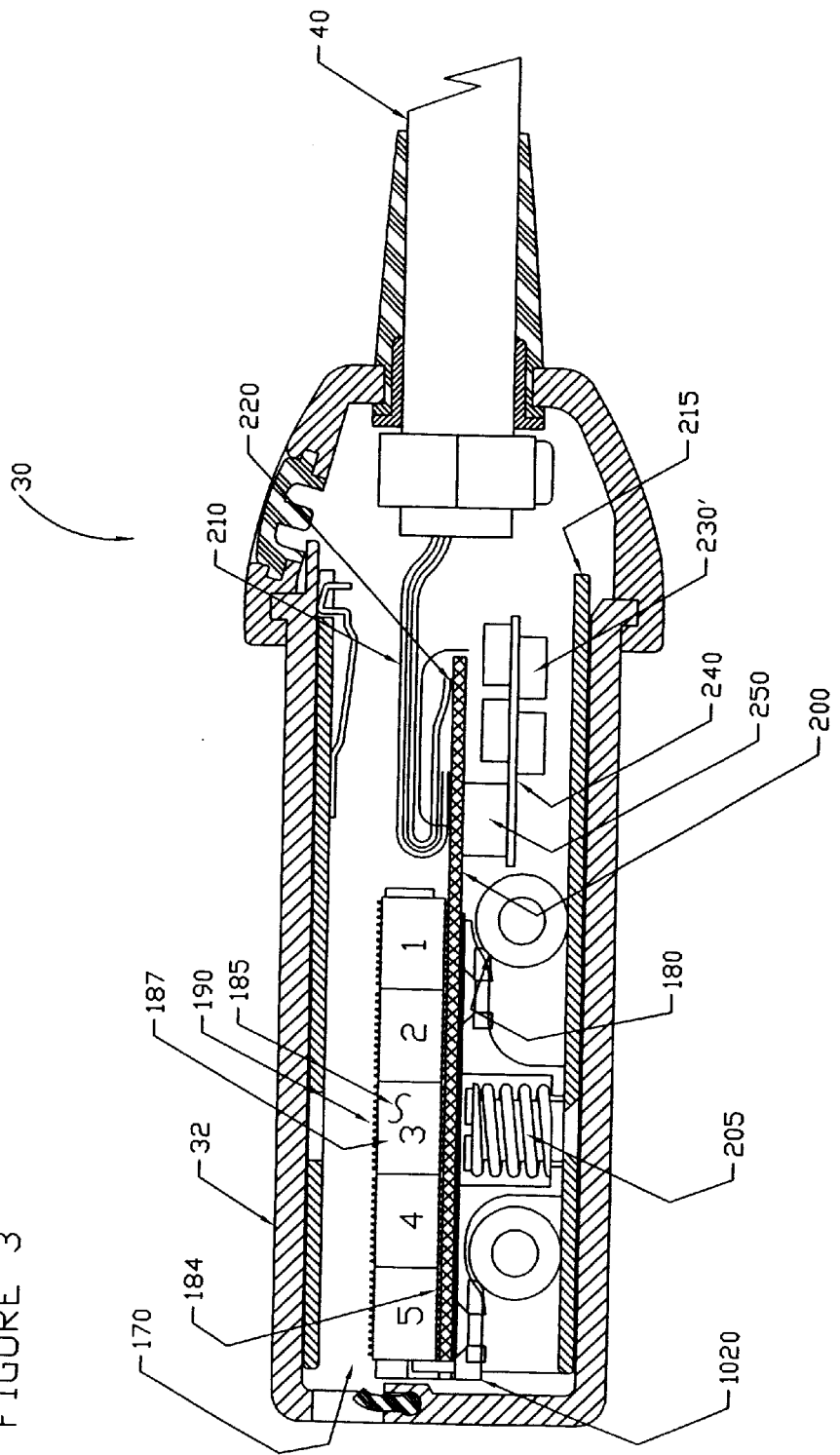
FIG. 3 is an illustration of a receptacle assembly of a preferred embodiment.

FIGS. 2 and 3 are detailed illustrations of the scan head 20 and receptacle assembly 30, respectively, of a presently preferred embodiment. As shown in FIG. 2, the exterior surface of the scan head 20 comprises a plastic housing 60, a nose piece 70, and an acoustic lens 80. Internal to the scan head 20 is an acoustic array of piezoelectric transducer elements 25 and a backing block 90, which is the mechanical foundation for the transducer array 25 and absorbs sound energy emitted from the back side of the array 25. A flexible circuit 100 carries a plurality of conductors, each conductor being electrically coupled with a respective transducer element in the transducer array 25. The flexible circuit 100 is coupled with a mezzanine printed wiring board 110 through an electrical interconnect 120. There are two mezzanine printed wiring boards in this preferred embodiment, and each is coupled with the other and to a scan head printed wiring board 130 via interfacing connectors 140. Printed wiring board 110 is called "mezzanine" because of its parallel, spaced arrangement with respect to the scan head printed wiring board 130. The scan head printed wiring board 130 is carried on a printed wiring board mount 150 and comprises a plurality of contact pads 160, which are preferably gold-plated contact pads.

Turning now to FIG. 3, the receptacle assembly 30 forms an opening 170 sized to receive the printed wiring board mount 150 (i.e., the part of the scan head that comprises the plurality of contact pads 160). The receptacle assembly 30 comprises five contact nest assemblies 185, each comprising 48 separate but identical contacts 190 and a molded plastic nest 187 with 48 apertures (not shown) designed to receive the contacts, inserted from the bottom. When properly seated within the molded plastic nest 187, each contact projects above the upper surface and projects below the lower surface. Each contact provides an electrical path between a contact pad on the scan head printed wiring board 130 and the corresponding contact pad on the receptacle printed wiring board 200 when the scan head 20 is fully inserted into the receptacle 30.

Each contact pad 184 on the receptacle printed wiring board 200 is electrically connected to a corresponding coaxial conductor interconnect pad 220 on the same board 200 through use of copper conductors within the printed wiring board 200. When properly terminated at the interconnect pads 220, the coaxial conductors 210 convey electrical signals from the contacts 190 to the connector 50 at the terminating end of the cable assembly 40, which mates with a port on the ultrasound system 55 or is hard wired to the ultrasound system 55. Thus, when the scan head 20 is fully inserted into the receptacle, there is an independent electrical path between individual elements in the scan head 25 and corresponding electrical circuits within the imaging system 55.

Figure 4:
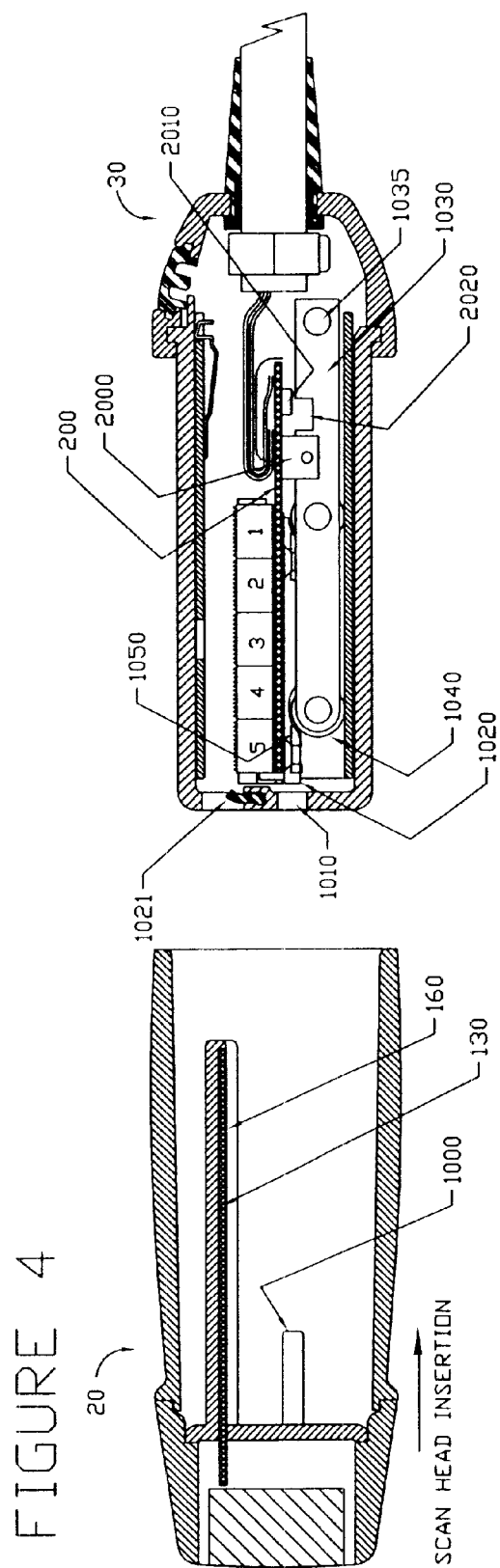
FIGS. 4–6 are illustrations of a scan head and a receptacle assembly of a preferred embodiment in separated, partially inserted, and fully inserted positions, respectively.

Interior to the housing 32 of the receptacle assembly 30 is a carriage assembly 1020, which comprises the five identical contact nest assemblies 185, linear cam surfaces 180, a carrier return spring 205, and the receptacle printed wiring board 200. Internal to the housing 32, but independent of the carriage assembly 1020, is a clamping sleeve 215 that is designed to slide along the axis of the housing 32, left to right in FIG. 3. The clamping sleeve is biased towards the left by a small spring (not shown). With reference to FIG. 4, internal to the housing 32 is a roller carrier 1030 with actuation rollers 1040. The roller carrier 1030 is kept stationary with respect to the housing 32 by an anchor pin 1035 that is fixed to the housing 32 with a feature not shown.

Figure 5:
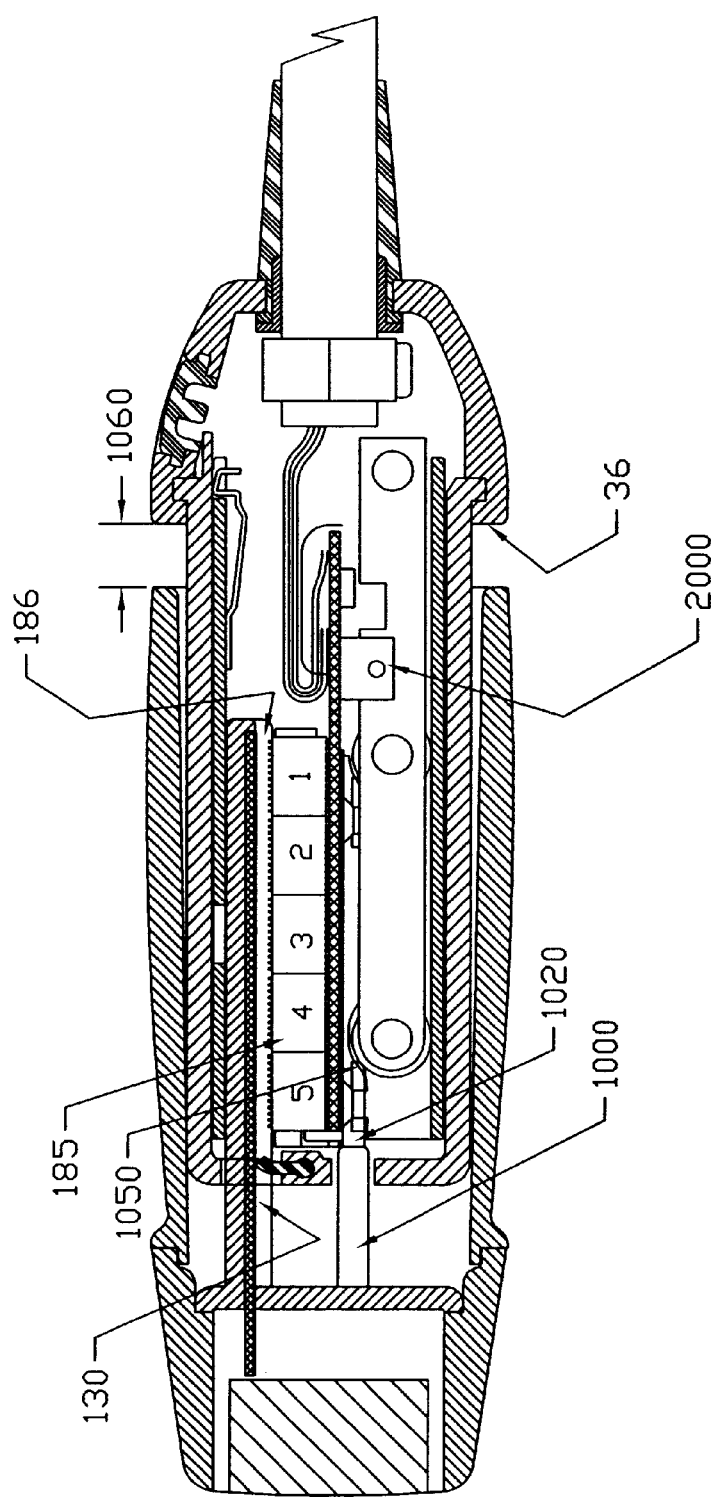
Figure 6:
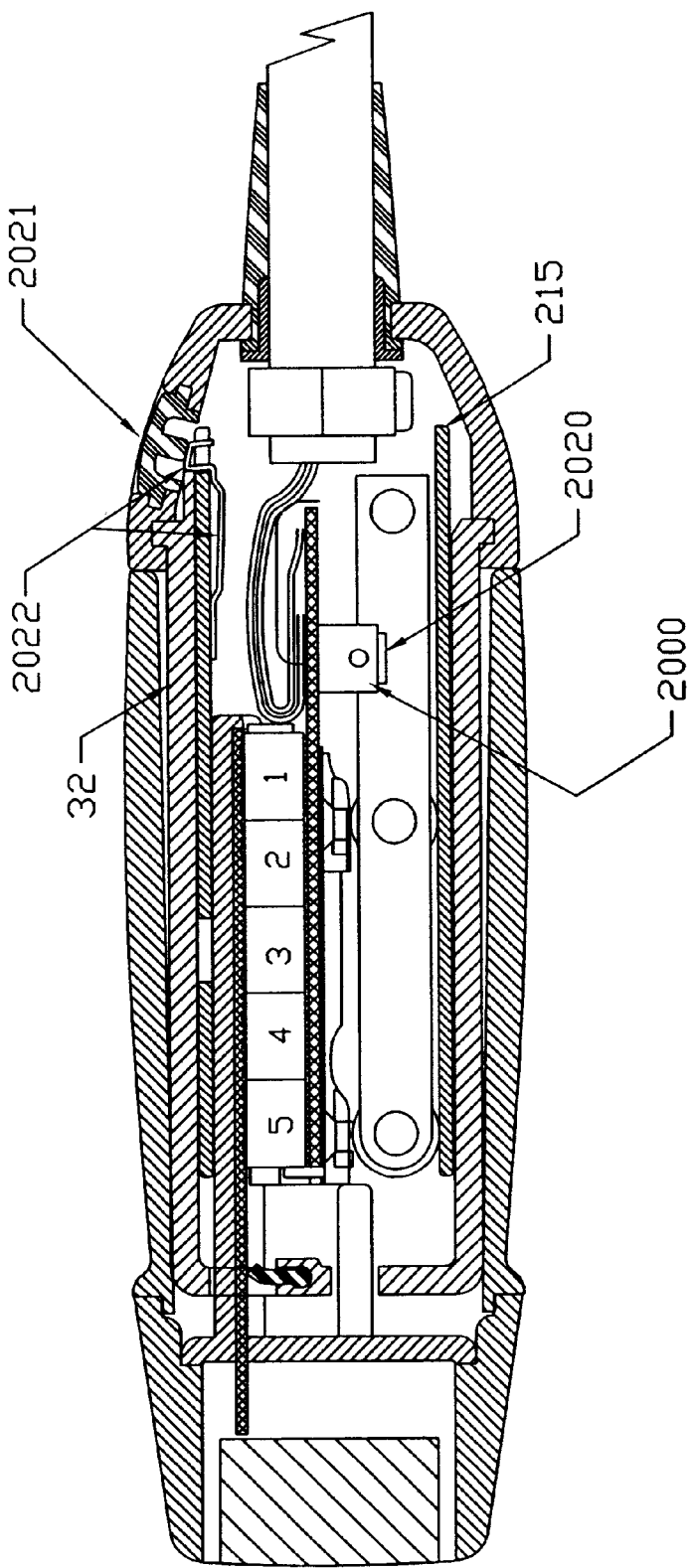

FIGS. 4–6 will now be used to describe the electrical and mechanical coupling of the scan head 20 and the receptacle assembly 30. Some components of the scan head 20 and the receptacle assembly 30 that were shown in FIGS. 2 and 3 have been removed from FIGS. 4–6 to simplify the drawings. FIG. 4 shows the scan head 20 and receptacle 30 separated from one another. Besides the components previously described, the scan head 20 comprises an actuator pin 1000. Further, the receptacle assembly 30 comprises an additional opening 1010 formed to receive the actuator pin 1000 and a rubber wiper 1021, designed to squeegee and displace any residual contamination on the surface of the printed wiring board 130.

As shown in FIG. 5, the scan head 20 can be inserted into the receptacle assembly 30 with zero insertion force until the actuator pin 1000 is inserted into opening 1010 and engages the edge of the carriage assembly 1020. At that point, the scan head 20 and receptacle assembly 30 are still not electrically coupled since there is a gap 186 between the contact nest assemblies 185 and the scan head printed wiring board 130. There is also a gap 1060 of about 0.200 inches between the edge of the scan head 20 and a raised portion 36 of the housing 32 of the receptacle assembly 30.

When the scan head 20 is further inserted into the receptacle assembly 30, the actuator pin 1000 pushes the carriage assembly 1020 to the right with respect to the stationary roller carrier 1030. When the cam surfaces 1050 of the carriage assembly 1020 engage the actuation rollers 1040, the carriage assembly 1020 moves upward (i.e., in a direction perpendicular to the scan head insertion direction). The upward movement of the carriage 1020 with respect to the clamping sleeve 215 causes the retraction spring 205 to compress. After the contacts 190 touch the contact pads 160 on the receptacle printed wiring board 130, further upward displacement of the carriage 1020 causes the contacts 190 to compress. The clamping force, which is required to compress the multitude of contacts 190, is generated by the cams 1050 riding up over the rollers 1040. As a result, reaction forces are generated between the rollers 1040 and the internal surface of the clamping sleeve 215 and between the opposite internal surface of the clamping sleeve 215 and the back surface of the printed wiring board mount 150, which is part of the scan head assembly 20. As insertion of the scan head assembly 20 continues, friction between the printed wiring board mount 150 and the clamping sleeve 215 cause them to move together (to the right in FIG. 5).

When the scan head 20 is fully inserted, the carriage assembly 1020 has moved about 0.200 inches to the right with respect to its initial position. When fully inserted, the spring locking pawl 2022, which is attached to inside of the clamping sleeve 215, engages the end of the housing 32. Due to the upward movement of the carriage assembly 1020, the multitude of electrically isolated contacts 190 in the contact nest assemblies 185 make mechanical contact with and are fully compressed against the pads on the scan head printed wiring board 130 (see FIG. 6). This results in an electrical interconnection between the scan head printed wiring board 130 and the receptacle printed wiring board 200, thereby electrically coupling the scan head 20 and the receptacle assembly 30. Additionally, the movement of the carriage assembly 1020 upward compresses (or clamps together) the contact nest assemblies 185 and the scan head printed wiring board 130, thereby mechanically coupling the scan head 20 and the receptacle assembly 30. In the fully inserted position shown in FIG. 6, the scan head 20 is ready to use.

To mechanically and electrically decouple the scan head 20 from the receptacle assembly 30, the rubber release button 2021 is pressed to cause the spring locking pawl 2022 to disengage from the end of the housing 32. The scan head 20 is then pulled out of the receptacle assembly 30. The carriage assembly 1020 is biased downward by the retraction spring 205. As the carriage assembly 1020 moves to the left, relative to the receptacle assembly 30, the cam surfaces 1050 ride down the actuator rollers 1040 and the carriage assembly 1020 moves downward away from the scan head printed wiring board 130, thereby both mechanically and electrically decoupling the scan head 20 and the receptacle assembly 30. The retraction spring 205 ensures that the contacts 190 will not be physically touching the contact pads 160 on the scan head printed wiring board 130 when the scan head 20 is withdrawn from the receptacle 30. It is important that the contacts 190 not drag across the contact pads 160 to preclude the possibility of physical damage to the contacts 190.

Embodiments Related to Imaging System Transmitter Control

The fact that the scan head 20 can be removed from the receptacle assembly 30 can create an undesirable electrical situation since the transmitters 59 in the ultrasound system 55 can provide transmit voltages of over 100 volts at the receptacle assembly 30. If the scan head 20 is not in the receptacle assembly 30, there is a chance that an operator or patient can come in contact with the high voltage present at the receptacle assembly 30. Further, attempts to clean the receptacle assembly 30 with electrically conductive disinfectants while the transmitters 59 are enabled can be particularly dangerous. In one preferred embodiment, to minimize the risk of electrical hazard, the transmitters 59 in the ultrasound system 55 are enabled only if the contacts 160 in the scan head 20 are electrically coupled with the contacts 190 in the receptacle assembly 30. In this way, high voltages are prevented from being present within the receptacle assembly 30 when a fault condition occurs (e.g., the scan head 20 is not properly engaged/fully seated/clamped in the receptacle assembly 30, when the scan head 20 is not present, etc.). This helps minimize the risk of an electrical hazard to the operator and also helps to minimize the risk of damage to the contacts.

A safety system that disables the transmitters 59 in the imaging system 55 can be implemented in any suitable manner. In one preferred embodiment, the receptacle assembly 30 contains components to determine when the contacts 160 in the scan head 20 are electrically coupled with the contacts 190 in the receptacle assembly 30. Turning again to FIG. 4, the receptacle assembly 30 comprises a detector, which here comprises an optical interrupter sensor 2000 and detection circuitry 2010 surface mounted on the receptacle printed wiring board 200. In one preferred embodiment, the sensor 2000 is an Omron EE-SX4070 optical detector. The "detector" can contain different or additional components. For example, a mechanical sensor, such as a small, mechanically actuated switch, can be used instead of an optical sensor. The detection circuitry 2010 is coupled with at least one conductor (preferably, two conductors) in the cable assembly 40 via the electrical interconnect 220. This conductor(s), which is represented by conductor 42 in FIG. 1, is used to send a signal to the control circuitry 57 in the ultrasound system 55 to enable/disable the transmitters 59. In this way, conductor 42 can be considered a "clamping sense line." As used herein, "send a signal" can mean actually sending a signal or interrupting a signal that is otherwise being provided.

The sensor 2000 is positioned in an inverted-U shape around the stationary roller carrier 1030, with a light emitter on one side and a light detector on the other. As shown in FIGS. 4 and 5, before the scan head 20 is fully inserted into the receptacle assembly 30 (i.e., when the scan head is in an "unclamped configuration"), light emitted by the sensor 2000 strikes the frame of the stationary roller carrier 1030 and does not reach the light detector. In this situation, the detection circuitry 2010 sends an "unclamped" signal via conductor 42 to the control circuitry 57 in the ultrasound system 55, which keeps the transmitters 59 in a disabled state. As the scan head 20 continues to be moved into the receptacle assembly 30, the optical path remains blocked by the frame of the stationary roller carrier 1030. However, there is a opening (a "sense slot" 2020) provided in the frame of the stationary roller carrier 1030. As the clamping action nears completion, the sensor 2000 passes next to the sense slot 2020, and an optical path is created between one side of the sensor 2000 and the other. When the optical path is created, the detection circuitry 2010 sends a "clamped state" signal to the control circuitry 57 of the imaging system 55 via line 42. The control circuitry 57 then enables the transmitters 59, and voltages are applied to the receptacle assembly 30.

Disengagement of the scan head 20 from the receptacle assembly 30 is accomplished by pulling the scan head 20 to the left. As the optical sensor 2000 passes the edge of the frame of the stationary roller carrier 1030, the optical path is again interrupted, and a "not ready" signal is conveyed to the ultrasound system 55. The control circuitry 57 disables the transmitters 59 in response to this signal. The transmitters 59 are preferably disabled before the contacts in the scan head 20 and receptacle assembly 30 are electrically decoupled. Disabling the transmitters 59 before the electrical contact is unloaded helps ensure that no destructive discharge will occur between the contacts of the scan head 20 and receptacle assembly 30 when the contact forces are negligible (during unlocking). The arcing problem is particularly acute when inductors are used at either the system connector end of the cable assembly 40 or at the scan head 20 since inductors store energy that causes a high voltage spike at the point where the circuit is opened. Accordingly, disabling the transmitters 59 upon detection of the scan head 20 being removed from the receptacle assembly 30 increases the durability of the electrical interface between the scan head 20 and the receptacle assembly 30. Disabling the transmitters 59 before contact unloading occurs can be accomplished by positioning the sensor 2000 with respect to the sense slot 2020 such that the optical path is broken by the frame of the stationary roller carrier 1030 before the contacts of the scan head 20 and the receptacle assembly 30 are electrically decoupled. In this way, the sensor 2000 detects the movement of the clamping mechanism, which is required before the contacts of the scan head 20 and the receptacle assembly 30 are electrically decoupled.

Embodiments Related to Multiplexing

Using a scan head with more transducer elements than system channels can be an important tool for improving image quality. Multiplexing is commonly used in ultrasound imaging systems to reduce the number of circuits required to support a given transducer configuration. For example, a transducer array of 256 or 128 active elements can be supported by an imaging system with only 64 active transmit and receive channels through the use of high-speed electrical switches in the imaging system. Essentially, high-speed switches in the imaging system connect the transmitters/receivers to a section of the array. Unfortunately, this approach results in an increase in the size of the cable assembly due to the added number of conductors (e.g., from 64 to 128 or 256), which makes the cable assembly less flexible. This approach also results in an increase in the size and mechanical complexity of the receptacle assembly due to the increased number of contacts.

In one preferred embodiment, instead of integrating the multiplexer in the ultrasound system, the multiplexer is integrated in the scan head. Integrating the multiplexer in the scan head provides the same advantages of using a multiplexer in the ultrasound system without the disadvantage of an increase in the size of the cable assembly. In this way, a multiplexer in the scan head allows a given cable assembly (e.g., of 64 individual coaxial conductors) to support larger arrays of piezoelectric elements. Integrating the multiplexer in the scan head also requires fewer number of contacts to support a given scan head and requires a less complex clamping system, as compared to the approach using a multiplexer in the ultrasound system. Accordingly, this preferred embodiment results in lower costs for the cable and receptacle assemblies, a smaller, more flexible cable assembly, and a smaller, more ergonomic receptacle assembly. Further, this preferred embodiment allows less-costly imaging systems with a limited number of processing channels (e.g., 64) to support higher resolution scan heads with vastly more piezoelectric elements (e.g., 128 or 256). In this way, improved diagnostic images can be obtained without redesigning the imaging system.

Figure 7:
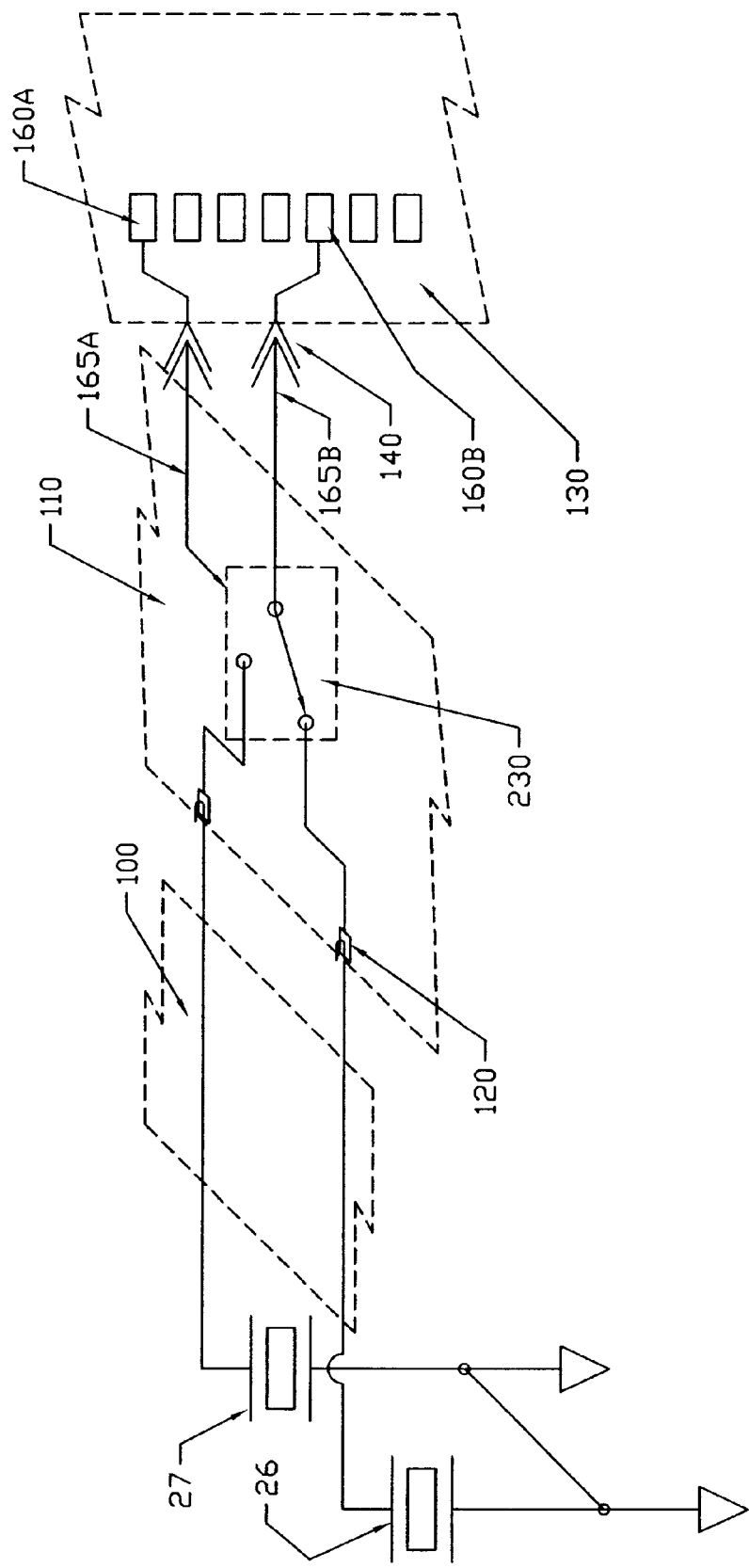
FIG. 7 is an electrical diagram of scan head multiplexing of a preferred embodiment.

In one preferred embodiment, the multiplexer is implemented as a surface-mounted switches 230 on the mezzanine printed wiring board 110 of the scan head 20 (see FIG. 2). FIG. 7 is an electrical diagram of this configuration. In this embodiment, the scan head 20 contains a linear array of 128 piezoelectric crystals (for simplicity, only a single low channel element 26 and high channel element 27 are shown), and the ultrasound system contains 64 channels. Accordingly, the number of conductors in the flexible circuit 100 (128) is more than the number of contacts 160 (64). In operation, the multiplexer 230 electrically couples either high channel elements (e.g., elements 65 thru 128), low channel elements (e.g., 1 thru 64), or any contiguous 64-channel section of the array to the 64 conductors within the cable assembly 40. The multiplexer switching is preferably controlled by the imaging system as part of its function to generate a coherent image from the whole transducer array 25. For example, a contact pad 160A and conductor 165A can be used to control the multiplexer 230, and other contact pads (such as contact pad 160B) and conductors (such as conductor 165B) can be used to communicate signals between the selected transducer elements and the ultrasound system.

In an alternate embodiment, instead of integrated the multiplexer in the scan head, the multiplexer is integrated in the receptacle assembly. In this embodiment, there are fewer conductors 210 (64) than there are contacts 190 (128) in the receptacle assembly 30, and the multiplexer electrically couples 64 of the contacts 190 with the 64 conductors 210. With reference to FIG. 3, the multiplexer can be implemented as a surface-mounted switch 230' on a mezzanine board 240, which is coupled with the receptacle printed wiring board 200 via an interfacing connector 250. As with the embodiment where the multiplexer is integrated in the scan head, this embodiment provides the advantage of reducing the number of coaxial conductors 210 in the cable assembly 40, thereby decreasing the size, cost, and complexity of the removable scan head 30. However, with this embodiment, the overall volume of the scan head/receptacle assembly will probably be greater because of the number of contacts and the complexity of the mechanical clamping system.

With either of these embodiments, any suitable technology can be used to implement a multiplexer. For example, both solid-state switches and very fast mechanical relays can be used. Suitable electronic switches include those based on C-MOS technology, such as a Supertex #HV20820 switch. These devices have been traditionally used within the imaging system to accomplish the multiplexing function. One disadvantage of solid-state switches is that the electrical resistance across the closed switch is between 15 and 22 ohms. Resistive losses within the switches reduces the ability of the imaging system to depict anatomical structures, particularly deep within the body. Another disadvantage of these devices is their size and their heat generation, both of which are important considerations in the design of an acceptable modular transducer system. Recently, very fast mechanical relays based on integrated circuit fabrication technologies have become available. These relays are called micro-electromechanical system (MEMS) devices and are now available from a number of vendors including Analog Devices in Massachusetts. A MEMS switch is an electrostatically operated mechanical relay. The use of integrated circuit fabrication techniques has allowed the relay to be scaled down so that a multitude of relays can be incorporated into a very small volume, such as that of a scan head. An important characteristic of this switch is the very small switching times when compared to a normal mechanical relay, which is a prime requirement for multiplexing. Another important feature of a MEMS device is its very low electrical resistance in the closed switch configuration. This overcomes a major shortcoming of a solid-state switch since low resistance results in higher acoustic performance and less heat generation within the scan head.

Embodiments Related to Optimizing Performance

Generally, there can be a significant mismatch in electrical impedance between each piezoelectric element of the transducer array and its corresponding coaxial conductor within the cable assembly. This impedance mismatch causes a loss of energy during transmit and attenuation of the receive signal detected by the imaging system. This results in less penetration and a reduction in the signal-to-noise ratio. Conventionally, a cable assembly is chosen for optimum performance with a particular acoustic array. However, with the modular transducer system, choosing the appropriate cable assembly is not an option since a single cable assembly supports any number of scan heads. Since cable characteristics such as impedance and D.C. resistance are important to the performance that can be achieved with a linear array of piezoelectric elements within the scan head, achieving optimum acoustic performance with each scan head can be a challenge.

Figure 8:
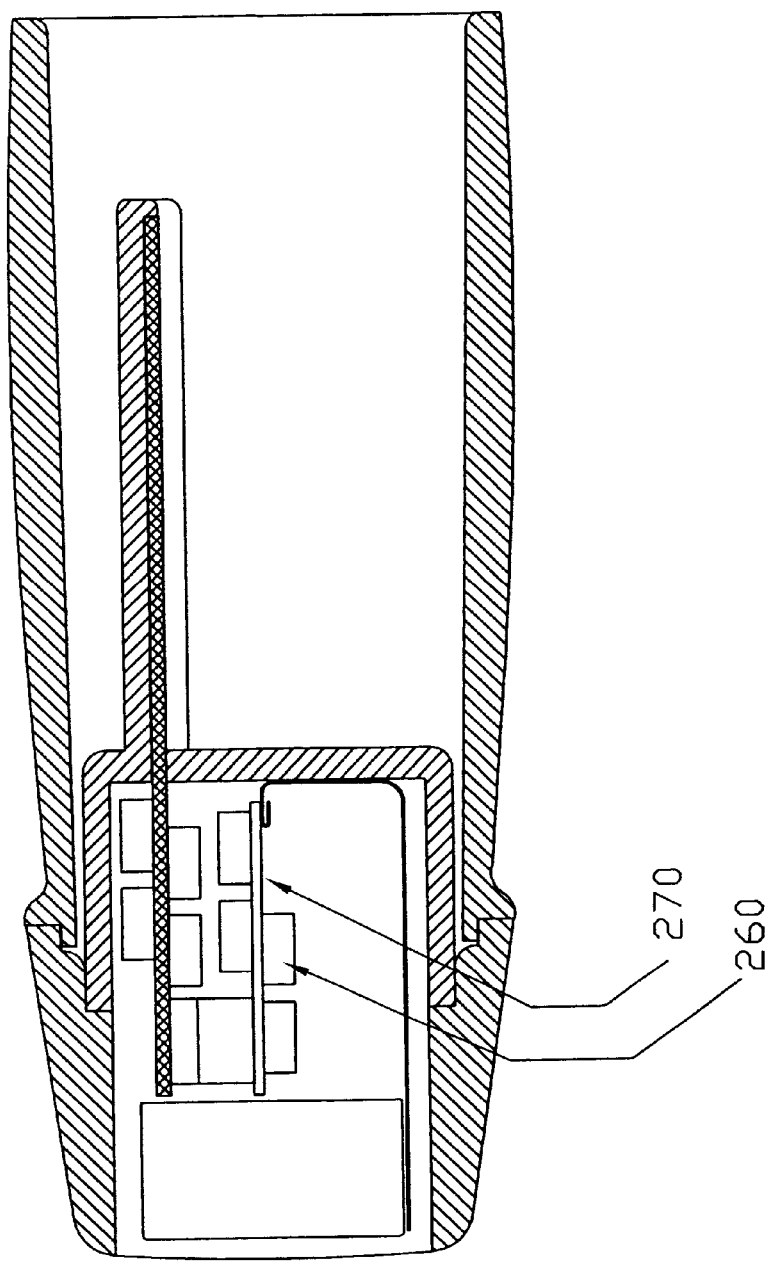
FIG. 8 is an illustration of a scan head of a preferred embodiment comprising active or passive components.

This preferred embodiment addresses the mismatch that can exist in electrical impedance between each transducer element and its corresponding conductor in the cable assembly by providing circuitry in the scan head that is operative to compensate for the mismatch in electrical impedance by increasing energy transfer between the transducer array and the conductors in the cable assembly. In this embodiment, the circuitry takes the form of surface-mounted passive or active components 260 on the mezzanine printed wiring board 270 of the scan head 20 (see FIG. 8). The circuitry can include, for example, an active component (e.g., an amplifier) and/or passive reactive components (e.g., capacitors or inductors). It is important to note that any suitable circuitry can be used to achieve this result, and the following claims should not be limited by the examples given herein.

Figure 9:
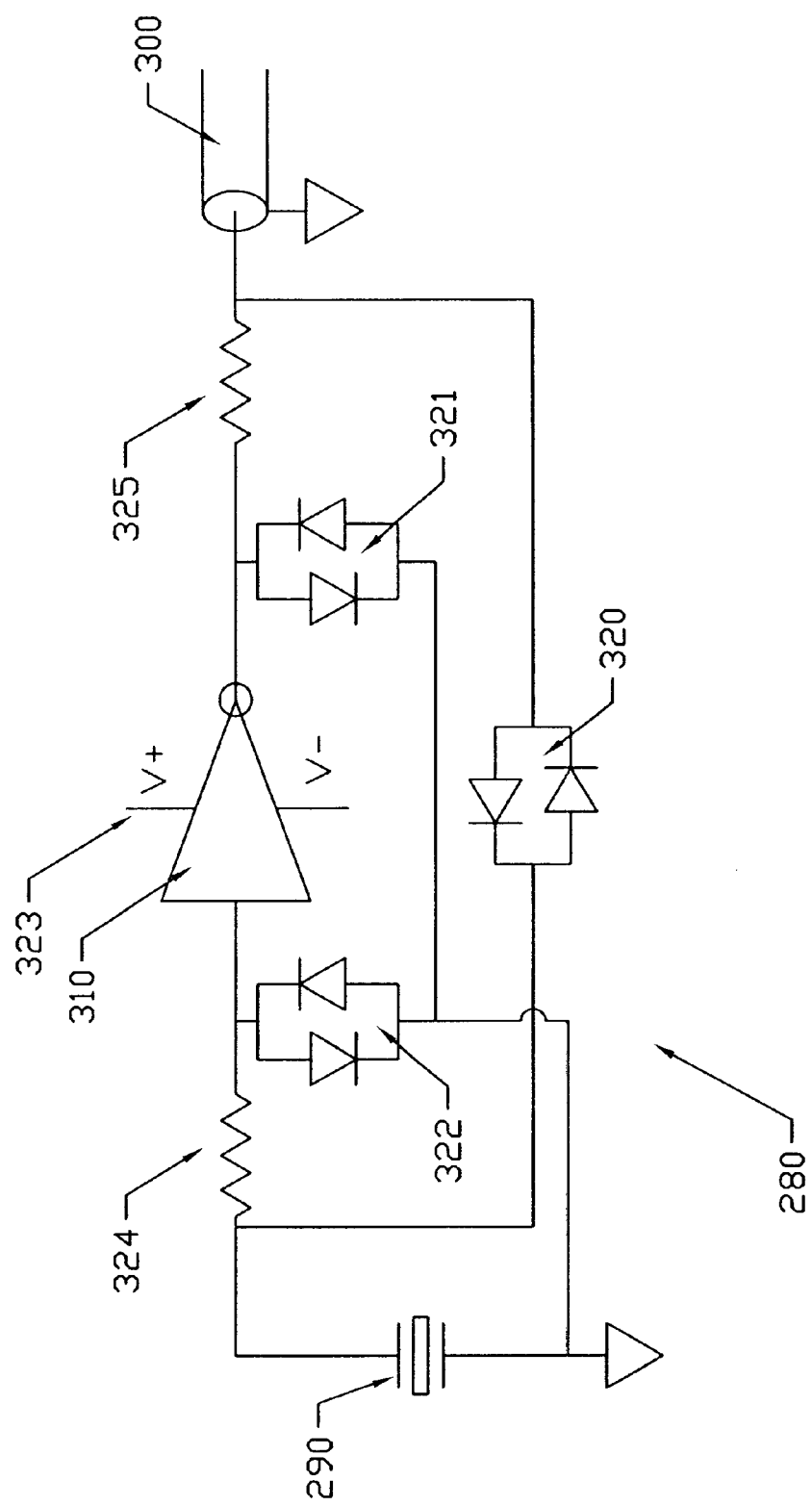
FIG. 9 is a diagram of a scan head of a preferred embodiment in which an amplifier is interposed between a transducer element and its corresponding coaxial conductor in a cable assembly.

FIG. 9 is a diagram of one possible embodiment of the circuitry 280. For simplicity, FIG. 9 shows only a single transducer element 290 and its corresponding coaxial conductor 300 in the cable assembly. In this embodiment, the transducer element 290 has an impedance of 400 ohms, and the coaxial conductor 300 has an impedance of 50 ohms. This impedance mismatch will result in loss in energy transfer, particularly in the receive mode. The resultant decrease in signal-to-noise ratio for the transducer assembly results in sub-optimal imaging performance, especially with respect to depicting details of organs deep within the body. To increase the energy transfer between the transducer element 390 and the conductor 300, the circuitry 280 comprises an amplifier 310 to increase the signal level into the conductor 300 during receive or to closely match the output impedance of the amplifier 310 to the impedance of the conductor 300. Supporting circuitry comprises a pair of diodes 320, which allow the transmit signal from the conductor 300 to bypass the amplifier 310 on the way to the transducer element 290. Diode pair 322 and resistor 324 prevent the input of amplifier 310 from exceeding the allowable voltage limits during transmit. Similarly, diode pair 321 and resistor 325 prevent the output of amplifier 310 from exceeding the allowable voltage limits during transmit.

Figure 10:
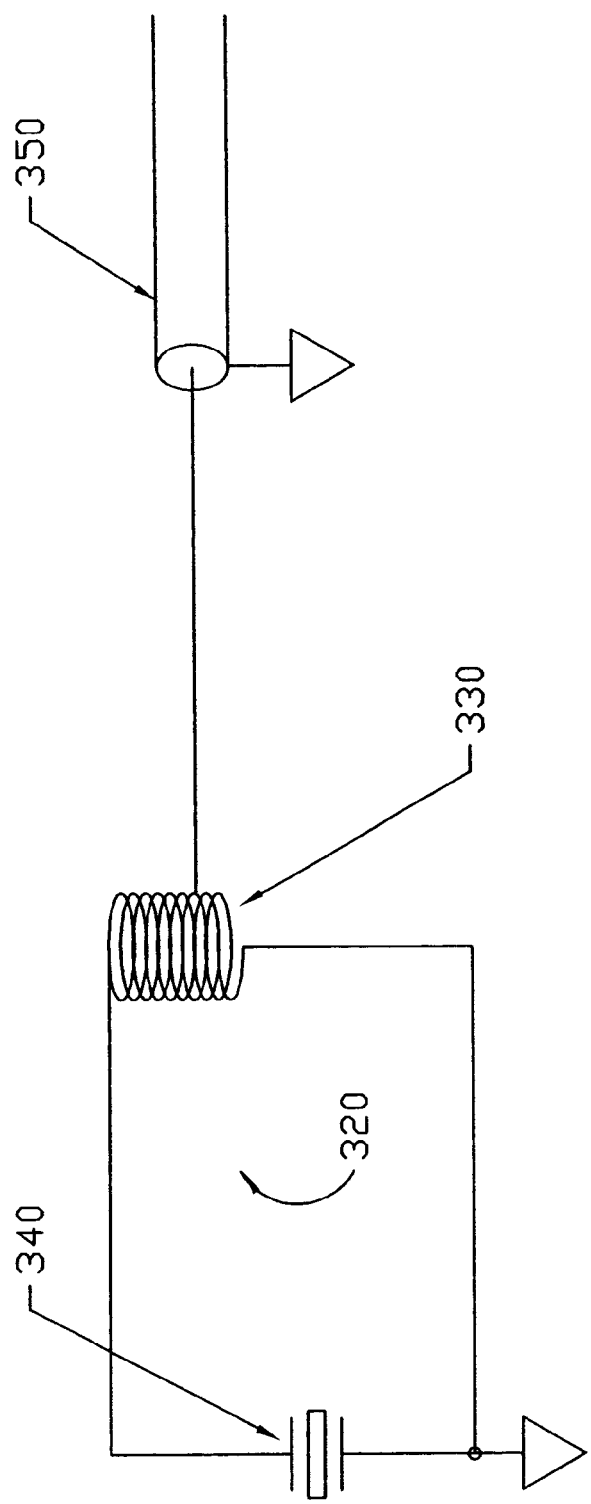
FIG. 10 is a diagram of a scan head of a preferred embodiment in which an auto-transformer is interposed between a transducer element and its corresponding coaxial conductor in a cable assembly.

In another embodiment, instead of an amplifier, the circuitry 320 comprises an auto-transformer 330 (see FIG. 10). The auto-transformer 330 is selected to maximize the energy transfer between the transducer element 340 and its corresponding coaxial conductor 350 in the cable assembly. In this embodiment, the transducer element 340 has an impedance of 400 ohms, the coaxial conductor 350 has an impedance of 50 ohms, and the auto-transformer 330 has a turn ratio of 8:1. During transmit, this arrangement can be expected to increase the maximum voltage at the transducer element 340, thereby increasing the amount of ultrasound energy projected into the body. This can be expected to increase the signal-to-noise ratio seen by the imaging system. During receive, this arrangement can be expected to reduce the fraction of signal lost along the capacitive coaxial inductor.

Figure 11:
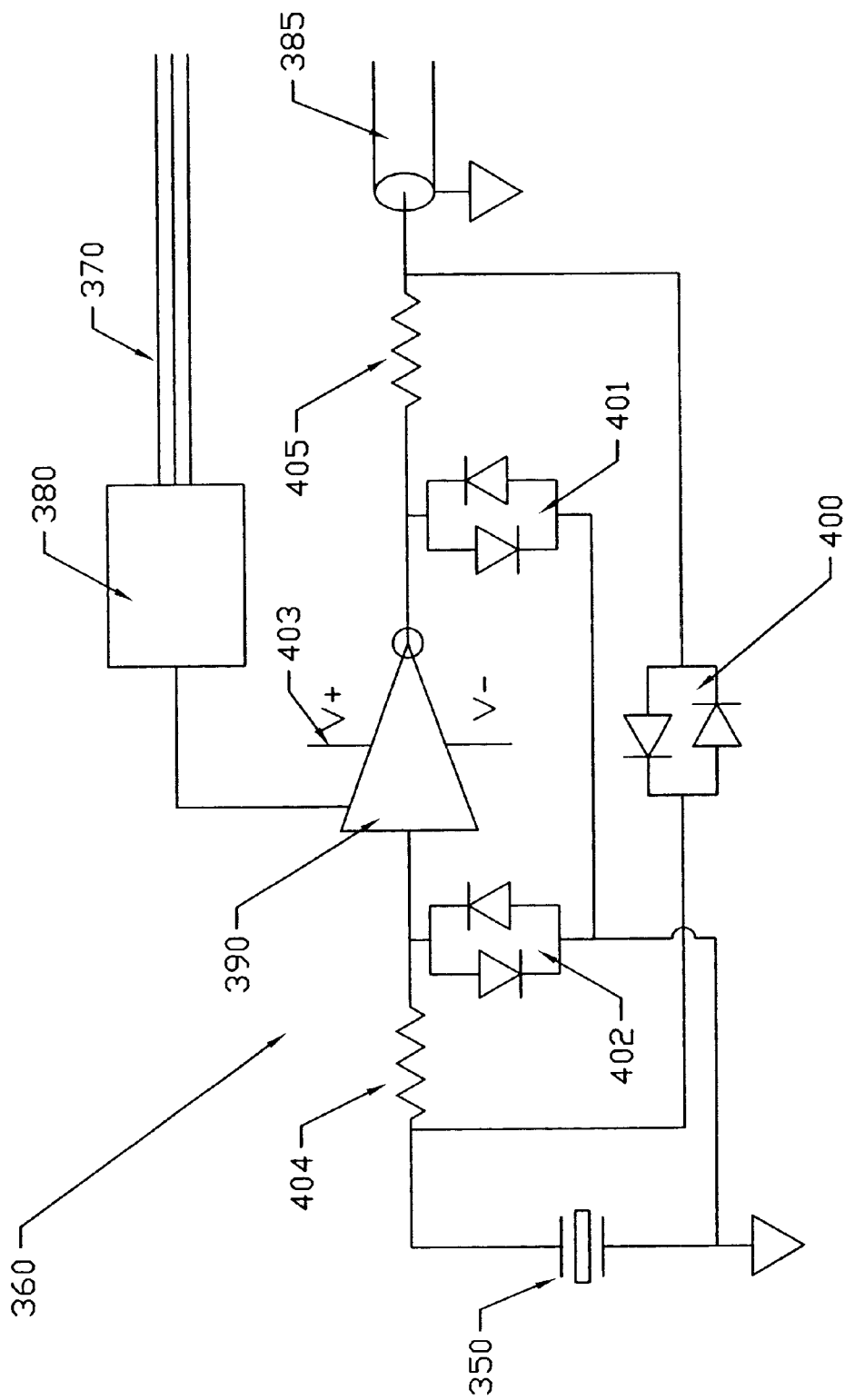
FIG. 11 is a diagram of a scan head of a preferred embodiment in which circuitry in the scan head is used to change frequency response characteristics of a transducer array.

In addition to or instead of increasing energy transfer, circuitry in the scan head can be used to change the frequency response characteristics of the transducer array. For example, the circuitry can be used to form a programmable band pass filter under the control of the imaging system. FIG. 11 is a diagram of one possible implementation of the circuitry 360 for a filter. Here, control signals 370 from the imaging system feed into a digital decoder 380, which controls an amplifier 390. Supporting circuitry comprise a pair of diodes 400 which allow the transmit signals from the conductor 385 to bypass the programmable amplifier 390 on the way to the transducer element 350. Diode pair 402 and resistor 404 prevent the input of the programmable amplifier 390 from exceeding the allowable voltage limits during transmit. Similarly, diode pair 401 and resistor 405 prevent the output of the programmable amplifier 390 from exceeding the voltage limit during transmit. The objective is to optimize the performance of the acoustic array/imaging system over a wide range of operating frequencies and imaging modalities. For example, in harmonic imaging, one frequency is used for transmit and another frequency (a multiple of the transmit frequency) is used for receive. Programmable frequency response characteristics in the scan head 20 can thus be expected to improve the diagnostic utility of the modular transducer system. This will be illustrated in conjunction with FIGS. 12 and 13.

Figure 12:
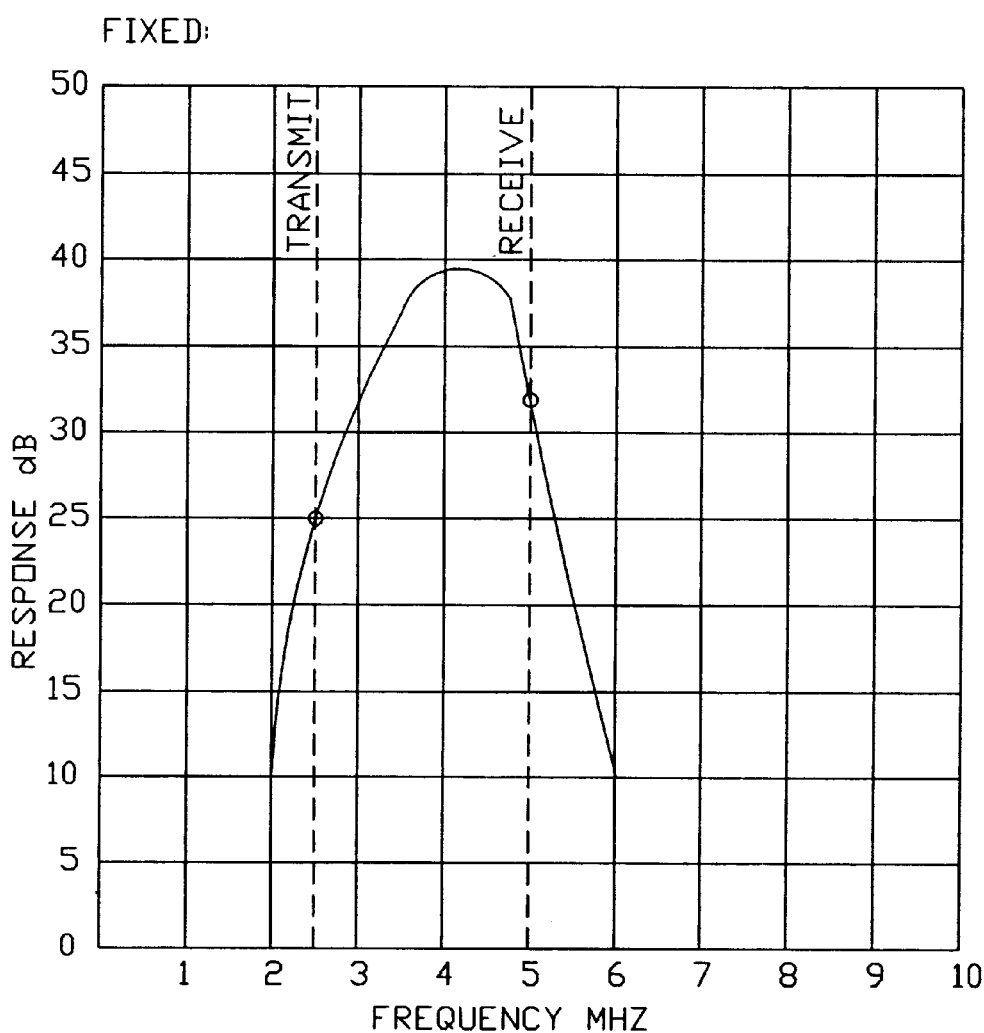
FIG. 12 is a graph of a fixed frequency response curve.
Figure 13:
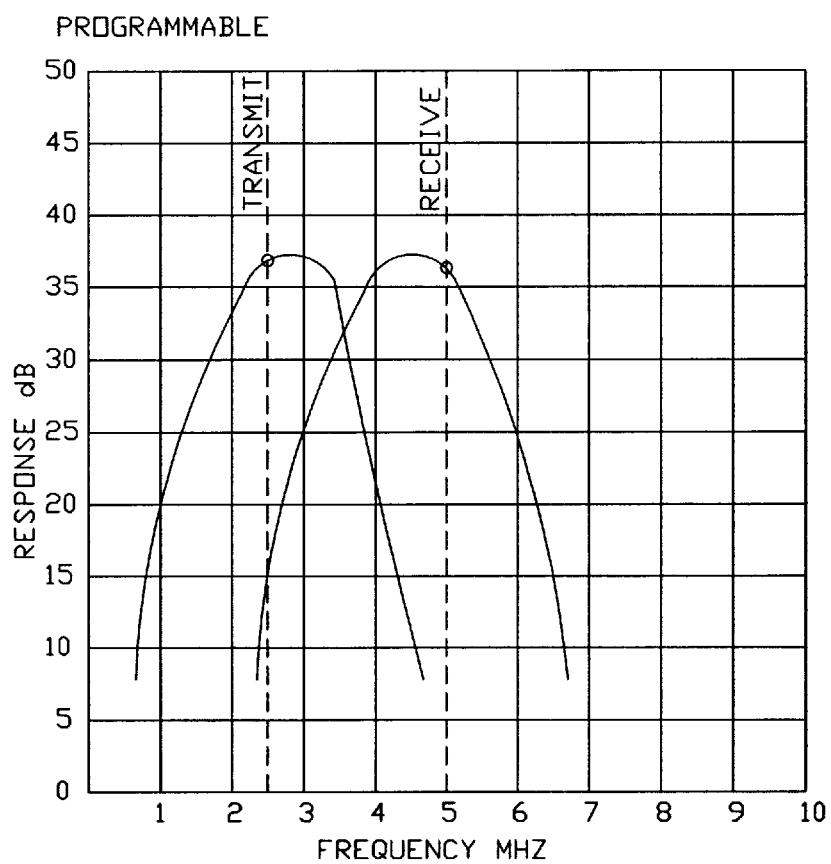
FIG. 13 is a graph of a programmable frequency response curve.

FIGS. 12 and 13 are graphs of fixed and programmable frequency response curves, respectively, and will be used to show the advantages of a programmable frequency response curve in harmonic imaging where the transmit frequency is 2.5 MHz and the receive frequency is 5.0 MHz. For this imaging approach, the transducer acoustic frequency response designed into the array of piezo-electric elements is sub-optimal for both transmit and for receive. The design of the acoustic array has an optimum operating frequency of about 4.1 MHz for transmit and receive, but with harmonic imaging, transmit occurs at 2.5 MHz where the sensitivity is 14 db down from maximum, and receive occurs at 5.0 MHz where the sensitivity is 7 db down. The result is that there is less ultrasound energy projected into the body with the acoustic array and less electrical signal generated when the array intercepts energy reflected from the internal structure of the body. This limits the ability of the imaging system to depict subtle details of organs deep within the body.

The advantage of using a programmable amplifier for the receive signals is depicted in FIG. 13. In this case, the acoustics design of the stack is optimized for about 3 MHz. This allows more energy to be projected into the body from the array of piezo-electric elements during transmit at 2.5 MHz, but the receive sensitivity at 5 MHz is reduced as a result of the array being optimized for 3 MHz operation. The receive sensitivity can be adjusted from the imaging system to increase the amplitude of the signals passed on to the imaging system at 5 MHz to compensate from the reduced sensitivity of the array of piezo-electric elements at that frequency. Accordingly, with a programmable frequency response curve, there is more power out during transmit and more sensitivity to reflected energy during receive.

Embodiments Related to Imaging System Interface Electronics within the Scan Head Generally, an imaging system must know the physical and acoustic characteristics of a transducer array before it can cause the array to project the required acoustic ultrasonic beam(s) within the body and before it can interpret the detected ultrasound reflections to form an image. Common practice is to store the characteristics of all transducers to be used with a particular imaging system within the system itself. The identification of the particular acoustic device that is active can be used by the imaging system to select the correct data set previously stored. Since the scan head in a modular transducer system is conveniently removable from the receptacle, it is preferred that the imaging system be capable of detecting the identity of the scan head in order to properly support it. One way in which to achieve this purpose is by providing circuitry integrated into the removable scan head, such as, for example, eight dedicated hardwired contact pads on the scan head printed wiring board. Depending on the identification code, certain contact pads would be electrically tied to ground while the remaining would be floating to create a code readable by the imaging system. A similar method has been used in the "AcuNav" ultrasound catheter product manufactured by the assignee of the present application.

Figure 14:
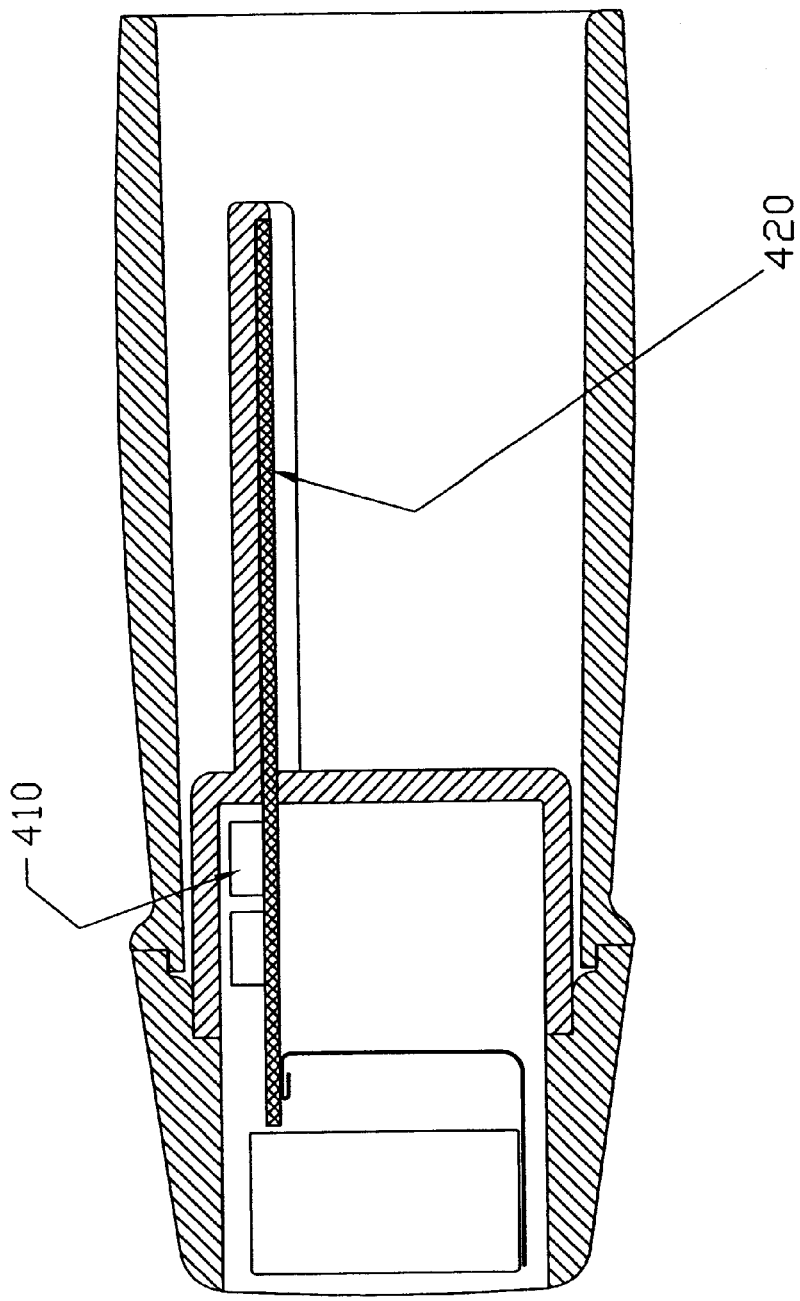
FIG. 14 is an illustration of a scan head of a preferred embodiment comprising a non-volatile memory device.

In this preferred embodiment, a non-volatile memory device is provided in the scan head. As shown in FIG. 14, the non-volatile memory device 410 can be surface mounted to the printed wiring board 420 in the scan head 20. The ultrasound system can read data stored in the non-volatile memory device and/or store data in the non-volatile memory device. A non-volatile memory device located in the scan head can be exploited to store scan head identification and serial number information. This memory can be interrogated by the imaging system to identify the scan head that is plugged into the receptacle assembly. This is a more sophisticated approach than that described above. A non-volatile memory device can be used to store far more than a scan head's identification. For example, all the micro-code used by the imaging system to properly operate the scan head can be downloaded from the non-volatile memory device every time it is used. An important advantage is.that the micro-code that is programmed into the non-volatile memory device when the scan head is manufactured can be optimized using physical test data from that particular device. In this way, the imaging system is optimized for the individual characteristics of the actual scan head, not some average established for that particular type of scan head. The increased performance can be interpreted as a more useful diagnostic image presented by the system display.

A non-volatile memory device in the scan head can also be used to store the imaging system settings last used with that particular device. During initialization, this information can be used by the imaging system to return it to the previous settings, which can reduce the time required to get a high quality diagnostic image. Additionally, a non-volatile memory device can be used to archive the use of the scan head. This feature can be used to support a new business model since lease charges can be keyed to the usage of the scan head. An archive of scan head use is also desirable whenever it is refurbished or replaced. A better understanding of how a failed device was used will result in better product designs in the future. U.S. patent application Ser. No. 10/185,217; filed on the same day as the present application), which is assigned to the assignee of the present invention and is hereby incorporated by reference, contains embodiments that can be used with the embodiments described herein.

It is preferred that the non-volatile memory device be a flash memory device, such as the CAT24WC02J flash memory device manufactured by Catalyst Semiconductor. That memory device is a two Kbit device, which is an eight pin S08 package. Data is programmed or retrieved from the device using a serial interface, which minimizes the number of conductors and contact pads required for implementation. Flash memory devices with more than one Mbyte are preferably used if micro-code is to be stored in the scan head.

It should be noted that the term "contact" is used in the following claims to broadly refer to an element that permits a flow of current. A "contact" can take the form of, but should not be limited to, the contacts and/or contact pads described above.

It is intended that the foregoing detailed description be understood as an illustration of selected forms that the invention can take and not as a definition of the invention. It is only the following claims, including all equivalents, that are intended to define the scope of this invention.

What is claimed is:

1. A modular transducer system comprising:
   a scan head comprising:
      a transducer array comprising a plurality of transducer elements;
      a plurality of conductors, each electrically coupled with a respective transducer element of the transducer array; and
      a first plurality of contacts, each electrically coupled with a respective conductor of the plurality of conductors;
   a receptacle assembly forming an opening sized to receive part of the scan head that comprises the first plurality of contacts, wherein the receptacle assembly comprises:
      a second plurality of contacts that mate with the first plurality of contacts;
      a member carrying the second plurality of contacts, the member movable between first and second positions, wherein the first and second plurality of contacts are electrically coupled when the member is in the second position; and
      a detector operative to detect when the member is in the second position; and
   a cable assembly electrically coupling the receptacle assembly with a medical diagnostic ultrasound imaging system;
   wherein the detector in the receptacle assembly sends a signal to the medical diagnostic ultrasound imaging system when the member is in the second position, and wherein the medical diagnostic ultrasound imaging system enables a set of transmitters in response to the signal.

2. The invention of claim 1, wherein the detector comprises an optical sensor.

3. The invention of claim 1, wherein the scan head further comprises an actuator pin, and wherein insertion of the actuator pin into the receptacle assembly moves the member from the first position to the second position.

4. The invention of claim 1, wherein the member is movable over at least one roller.

5. The invention of claim 4, wherein the at least one roller is provided on a stationary roller carrier.

6. The invention of claim 5, wherein an opening is formed in the stationary roller carrier, wherein the detector comprises an optical sensor, wherein an optical path is blocked by the stationary roller carrier when the member is in the first position, and wherein an optical path is created through the opening formed in the stationary roller carrier when the member is in the second position.

7. The invention of claim 4, wherein the member comprises a cam surface, and wherein movement of the cam surface over the at least one roller causes the member to move in a direction perpendicular to a scan head insertion direction.

8. The invention of claim 1, wherein the cable assembly comprises a second plurality of conductors, wherein some of the conductors of the second plurality of conductors are electrically coupled with the second plurality of contacts, and wherein at least one additional conductor of the second plurality of conductors electrically couples the detector with a controller in the medical diagnostic ultrasound imaging system.

9. The invention of claim 1, wherein the detector in the receptacle assembly does not send the signal to the medical diagnostic ultrasound imaging system when the member is not in the second position, and wherein the medical diagnostic ultrasound imaging system disables the set of transmitters in response to not receiving the signal.

10. A method for medical diagnostic ultrasound imaging system transmitter control in a modular transducer system, the method comprising:

(a) providing a scan head comprising a transducer array comprising a plurality of transducer elements; a plurality of conductors, each electrically coupled with a respective transducer element of the transducer array; and a first plurality of contacts, each electrically coupled with a respective conductor of the plurality of conductors;

(b) providing a receptacle assembly forming an opening sized to receive part of the scan head that comprises the first plurality of contacts, the receptacle assembly comprising a second plurality of contacts that mate with the first plurality of contacts; and (c) enabling a set of transmitters in a medical diagnostic ultrasound imaging system electrically coupled with the receptacle assembly only if the first plurality of contacts in the scan head are electrically coupled with the second plurality of contacts in the receptacle assembly.

11. The invention of claim 10 further comprising before the first plurality of contacts in the scan head are electrically decoupled from the second plurality of contacts in the receptacle assembly, disabling the set of transmitters in the medical diagnostic ultrasound imaging system.

12. The invention of claim 10, wherein the second plurality of contacts are carried on a member movable in the receptacle assembly between first and second positions, wherein the first and second plurality of contacts are electrically coupled when the member is in the second position, and wherein the invention further comprises:

with a detector in the receptacle assembly, detecting when the member is in the second position;

sending a signal to the medical diagnostic ultrasound imaging system in response to the detector detecting that the member is in the second position; and enabling the set of transmitters in response to the signal.

13. The invention of claim 12, wherein the detector comprises an optical sensor.

14. A modular transducer system comprising:

a scan head comprising:
 a transducer array comprising a plurality of transducer elements;
 a plurality of conductors, each electrically coupled with a respective transducer element of the transducer array; and
 a first plurality of contacts, each electrically coupled with a respective conductor of the plurality of conductors;

a receptacle assembly forming an opening sized to receive part of the scan head that comprises the first plurality of contacts, wherein the receptacle assembly comprises:
 a second plurality of contacts that mate with the first plurality of contacts; and
 a detector operative to detect when the first and second plurality of contacts are electrically coupled; and a cable assembly electrically coupling the receptacle assembly with a medical diagnostic ultrasound imaging system;

wherein the detector in the receptacle assembly sends a signal to the medical diagnostic ultrasound imaging system when the detector detects that the first and second plurality of contacts are electrically coupled, and wherein the medical diagnostic ultrasound imaging system enables a set of transmitters in response to the signal.

15. The invention of claim 14, wherein the detector comprises an optical detector.

16. The invention of claim 14, wherein the second plurality of contacts are carried on a member movable in the receptacle assembly between first and second positions, wherein the first and second plurality of contacts are electrically coupled when the member is in the second position, and wherein the detector detects that the first and second plurality of contacts are electrically coupled by detecting when the member is in the second position.

17. The invention of claim 14, wherein the detector is operative to detect when the first and second plurality of contacts are going to be electrically decoupled, and wherein the medical diagnostic ultrasound imaging system disables the set of transmitters before the first and second plurality of contacts are electrically decoupled.

* * * * *